(12) United States Patent
Rajan et al.

(10) Patent No.: US 9,870,449 B2
(45) Date of Patent: Jan. 16, 2018

(54) METHODS AND SYSTEMS FOR PREDICTING HEALTH CONDITION OF HUMAN SUBJECTS

(71) Applicant: Conduent Business Services, LLC, Dallas, TX (US)

(72) Inventors: Vaibhav Rajan, Bangalore (IN); Abhishek Tripathi, Bangalore (IN); Sakyajit Bhattacharya, Bangalore (IN); Ranjan Shetty K, Parkala Udupi (IN); Amith Sitaram, Shimoga (IN); Vivek G Raman, Manipal (IN)

(73) Assignee: CONDUENT BUSINESS SERVICES, LLC, Dallas, TX (US)

( * ) Notice: Subject to any disclaimer, the term of this patent is extended or adjusted under 35 U.S.C. 154(b) by 408 days.

(21) Appl. No.: 14/629,766

(22) Filed: Feb. 24, 2015

(65) Prior Publication Data

US 2016/0246931 A1    Aug. 25, 2016

(51) Int. Cl.
| | | |
|---|---|---|
| *G06F 17/00* | (2006.01) | |
| *G06F 17/20* | (2006.01) | |
| *G06F 19/00* | (2011.01) | |
| *G06N 99/00* | (2010.01) | |
| *G06N 7/00* | (2006.01) | |

(52) U.S. Cl.
CPC .......... *G06F 19/345* (2013.01); *G06N 7/005* (2013.01); *G06N 99/005* (2013.01)

(58) Field of Classification Search
USPC ......................................................... 706/11
See application file for complete search history.

(56) References Cited

U.S. PATENT DOCUMENTS 8,065,742 B2 * 11/2011 Shukla ............... G02B 6/29374
                                                          726/28
8,699,486 B1 *  4/2014 Luo ......................... H04L 12/18
                                                          370/351

(Continued)

OTHER PUBLICATIONS

Development of Cardiac Prescreening Device for Rural Population Using Ultralow-Power Embedded System Subhamoy Mandal; Kausik Basak; K. M. Mandana; Ajoy K. Ray; Jyotirmoy Chatterjee; Manjunatha Mahadevappa IEEE Transactions on Biomedical Engineering Year: 2011, vol. 58, Issue: 3 pp. 745-749 IEEE Journals & Magazines.*

(Continued)

*Primary Examiner* — Michael B Holmes
(74) *Attorney, Agent, or Firm* — Jones Robb, PLLC

(57) ABSTRACT

Disclosed are methods and systems for classifying one or more human subjects in one or more categories indicative of a health condition of the one or more human subjects. The method includes categorizing one or more parameters of each of the one or more human subjects in one or more data views based on a data type of each of the one or more parameters. A data view corresponds to a first data structure storing a set of parameters categorized in the data view, associated with each of the one or more human subjects. The one or more data views are transformed to a second data structure representative of the set of parameters across the one or more data views. Thereafter, a classifier is trained based on the second data structure, wherein the classifier classifies the one or more human subjects in the one or more categories.

20 Claims, 12 Drawing Sheets

(56) References Cited

U.S. PATENT DOCUMENTS

| | | | |
|---|---|---|---|
| 9,159,032 B1* | 10/2015 | Tripathi | G06N 5/048 |
| 9,228,841 B2* | 1/2016 | Dutta | G01C 21/3605 |
| 9,305,245 B2* | 4/2016 | Tripathi | G06K 9/726 |
| 9,383,976 B1* | 7/2016 | Singh | G06F 8/34 |
| 9,471,876 B2* | 10/2016 | Bhattacharya | H04L 67/10 |
| 9,489,624 B2* | 11/2016 | Dasgupta | G06N 5/02 |
| 9,582,484 B2* | 2/2017 | Gajera | G06F 17/243 |
| 9,596,094 B2* | 3/2017 | Luo | H04L 12/18 |
| 2011/0070582 A1* | 3/2011 | Bankaitis-Davis | C12Q 1/6886 435/6.11 |
| 2013/0189243 A1 | 7/2013 | Barr et al. | |
| 2013/0262357 A1 | 10/2013 | Amarasingham et al. | |
| 2014/0024553 A1* | 1/2014 | Michalek | G01N 33/57423 506/9 |
| 2014/0045198 A1 | 2/2014 | Montaner Villalonga et al. | |
| 2014/0074509 A1 | 3/2014 | Amarasingham et al. | |
| 2014/0200824 A1 | 7/2014 | Pancoska | |
| 2016/0102150 A1* | 4/2016 | Sexton | C07K 16/40 424/9.2 |

OTHER PUBLICATIONS

Automated Detection of Instantaneous Gait Events Using Time Frequency Analysis and Manifold Embedding Min S. H. Aung; Sibylle B. Thies; Laurence P. J. Kenney; David Howard; Ruud W. Selles; Andrew H. Findlow; John Y. Goulermas IEEE Transactions on Neural Systems and Rehabilitation Engineering Year: 2013, vol. 21, Issue: 6 pp. 908-916 IEEE.*

Lossless Compression of RNAi Fluorescence Images Using Regional Fluctuations of Pixels Nader Karimi; Shadrokh Samavi; Shahram Shirani IEEE Journal of Biomedical and Health Informatics Year: 2013, vol. 17, Issue: 2 pp. 259-268 IEEE Journals & Magazines.*

Eissa A., Krass I., and Bajorek B. Optimizing the management of acute ischaemic stroke: a review of the utilization of intravenous recombinant tissue plasminogen activator (tpa). Journal of Clinical Pharmacy and Therapeutics, 37(6):620-629, 2012.

Furlan A, Higashida R, Wechsler L, and et al. Intra-arterial prourokinase for acute ischemic stroke: The proact ii study: a randomized controlled trial. JAMA, 282(21):2003-2011, 1999.

Lewandowski C A, Frankel M, Tomsick T A, and et al. Combined intravenous and intra-arterial r-tpa versus intra-arterial therapy of acute ischemic stroke. emergency management of stroke (ems) bridging trial. Stroke, 30:2598-2605, 1999.

Kannel W B, McGee D, and Gordon T. A general cardiovascular risk profile: the framingham study. American Journal of Cardiology, 38:46-51, 1976.

Guillaume Bouchard, Dawei Yin, and Shengbo Guo. Convex collective matrix factorization. In Proceedings of the Sixteenth International Conference on Articial Intelligence and Statistics, pp. 144-152, 2013.

J. Jaime Caro, Krista F. Huybrechts, Heather E. Kelley, and for the Stroke Economic Analysis Group. Predicting treatment costs after acute ischemic stroke on the basis of patient characteristics at presentation and early dysfunction. Stroke, 32(1):100-106, 2001.

Thomas J. DeGraba, John M. Hallenbeck, Karen D. Pettigrew, Andrew J. Dutka, and Brian J. Kelly. Progression in acute stroke: Value of the initial nih stroke scale score on patient stratication in future trials. Stroke, 30(6):1208-1212, 1999.

Gregory J. del Zoppo, Randall T. Higashida, Anthony J. Furlan, Michael S. Pessin, Howard A. Rowley, and Michael Gent. Proact: A phase ii randomized trial of recombinant pro-urokinase by direct arterial delivery in acute middle cerebral artery stroke. Stroke, 29(1):4-11, 1998.

Tracy D Farr and Susanne Wegener. Use of magnetic resonance imaging to predict outcome after stroke: a review of experimental and clinical evidence. Journal of Cerebral Blood Flow and Metabolism, 30:703-717, 2010.

Yangqing Jia, Mathieu Salzmann, and Trevor Darrell. Factorized latent spaces with structured sparsity. In NIPS, pp. 982-990, 2010.

Panel Margaret Kelly-Hayes, James T. Robertson, Joseph P. Broderick, Pamela W. Duncan, Linda A. Hershey, Elliot J. Roth, William H. Thies, and Catherine A. Trombly. The american heart association stroke outcome classication. 29(6):1274-1280, 1998.

Arto Klami, Guillaume Bouchard, and Abhishek Tripathi. Groupsparse embeddings in collective matrix factorization. http://arxiv.org/pdf/1312.5921v1.pdf, 2014.

Arto Klami, Seppo Virtanen, and Samuel Kaski. Bayesian canonical correlation analysis. The Journal of Machine Learning Research, 14(1):965-1003, 2013.

M R Law and N J Wald. Risk factor thresholds: their existence under scrutiny. BMJ, 324(7353):1570-1576, 6 2002.

Patrick Lyden, Mei Lu, Christy Jackson, John Marler, Rashmi Kothari, Thomas Brott, and Justin Zivin. Underlying structure of the national institutes of health stroke scale: Results of a factor analysis. Stroke, 30(11):2347-2354, 1999.

World Health Organization. The world health report 2000 { health systems: Improving performance. http://www.who.int/cardiovascular_diseases/en/cvd_atlas_15_burden_stroke.pdf.

World Health Organization. The world health report 2000 { health systems: Improving performance, 2000.

Andrea Rocco, Marta Pasquini, Emanuella Cecconi, Gaia Sirimarco, Maria C. Ricciardi, Edoardo Vicenzini, Marta Altieri, Vittorio Di Piero, and Gian L. Lenzi. Monitoring after the acute stage of stroke: A prospective study. Stroke, 38(4):1225-1228, 2007.

Gustavo Saposnik, Amy K. Guzik, Mathew Reeves, Bruce Ovbiagele, and S. Claiborne Johnston. Stroke prognostication using age and nih stroke scale: Span-100. Neurology, 2012.

Daniel Schlegel, Stephen J. Kolb, Jean M. Luciano, Jennifer M. Tovar, Brett L. Cucchiara, David S. Liebeskind, and Scott E. Kasner. Utility of the nih stroke scale as a predictor of hospital disposition. Stroke, 34(1):134-137, 2003.

Clark WM, Wissman S, Albers GW, and et al. Recombinant tissue-type plasminogen activator (alteplase) for ischemic stroke 3 to 5 hours after symptom onset: The atlantis study: a randomized controlled trial. JAMA, 282(21):2019-2026, 1999.

\* cited by examiner

FIG. 5A $$e_1 \underset{X_1}{\square} \; e_2 \underset{X_2}{\square} \; e_3 \underset{X_3}{\square} \; e_4 \quad \rightarrow \quad \begin{array}{c|c|c|c|c|} & e_1 & e_2 & e_3 & e_4 \\ \hline e_1 & ? & X_1 & X_2 & X_3 \\ \hline e_2 & X_1^T & ? & ? & ? \\ \hline e_3 & X_2^T & ? & ? & ? \\ \hline e_4 & X_3^T & ? & ? & ? \\ \hline \end{array} \quad = \quad [Y] \qquad (1)$$

FIG. 7

METHODS AND SYSTEMS FOR PREDICTING HEALTH CONDITION OF HUMAN SUBJECTS

TECHNICAL FIELD

The presently disclosed embodiments are related, in general, to a health condition diagnosis. More particularly, the presently disclosed embodiments are related to methods and systems for predicting health condition of human subjects.

BACKGROUND

With increasing complexity of the lifestyle of human beings, health-related issues, in general, have risen in the past few years. For instance, there has been a rise in cardio-vascular diseases, high blood pressure, and diabetes in young people. Developing a mathematical model that has the capability to predict the risk of such diseases/conditions might help the people to alter their lifestyles. Further, such predictions may help the doctors to provide consultations to such people, accordingly.

SUMMARY

According to embodiments illustrated herein there is provided a system for classifying one or more human subjects in one or more categories indicative of a health condition associated with the one or more human subjects. The system comprises one or more micro-processors configured to categorize one or more parameters associated with each of the one or more human subjects in one or more data views based on at least a data type of each of the one or more parameters. A data view corresponds to a first data structure storing a set of parameters categorized in the data view, associated with each of the one or more human subjects. The one or more micro-processors are further configured to transform one or more data views to a second data structure, wherein the second data structure is representative of the set of parameters across the one or more data views. The one or more micro-processors are further configured to train a classifier based on the second data structure, wherein the classifier classifies the one or more human subjects in the one or more categories. The system further comprises a transceiver configured to send the classification of the one or more human subjects in the one or more categories to a computing device, wherein the classification of the one or more human subjects is displayed on a display device of the computing device through a user-interface.

According to embodiments illustrated herein there is provided a method for classifying one or more human subjects in one or more categories indicative of a health condition associated with the one or more human subjects. The method includes categorizing, by one or more micro-processors, one or more parameters associated with each of the one or more human subjects in one or more data views based on at least a data type of each of the one or more parameters. A data view corresponds to a first data structure storing a set of parameters categorized in the data view, associated with each of the one or more human subjects. The method further includes transforming, by the one or more micro-processors, the one or more data views to a second data structure, wherein the second data structure is representative of the set of parameters across the one or more data views. The method further includes training, by the one or more micro-processors, a classifier based on the second data structure, wherein the classifier classifies the one or more human subjects in the one or more categories. The method further includes sending, by a transceiver, the classification of the one or more human subjects in the one or more categories to a computing device, wherein the classification of the one or more human subjects is displayed on a display device of the computing device through a user-interface.

According to embodiments illustrated herein there is provided a computer program product for use with a computing device. The computer program product comprising a non-transitory computer readable medium. The non-transitory computer readable medium stores a computer program code for classifying one or more human subjects in one or more categories indicative of a health condition associated with the one or more human subjects. The computer program code is executable by one or more micro-processors in the computing device to categorize one or more parameters associated with each of the one or more human subjects in one or more data views based on at least a data type of each of the one or more parameters. A data view corresponds to a first data structure storing a set of parameters categorized in the data view, associated with each of the one or more human subjects. The computer program code is further executable by the one or more micro-processors to transform the one or more data views to a second data structure, wherein the second data structure is representative of the set of parameters across the one or more data views. The computer program code is further executable by the one or more micro-processors to train a classifier based on the second data structure, wherein the classifier classifies the one or more human subjects in the one or more categories. The computer program code is further executable by the one or more micro-processors to send, by a transceiver, the classification of the one or more human subjects in the one or more categories to a second computing device, wherein the classification of the one or more human subjects is displayed on a display device of the second computing device through a user-interface.

BRIEF DESCRIPTION OF DRAWINGS

The accompanying drawings illustrate various embodiments of systems, methods, and other aspects of the disclosure. Any person having ordinary skill in the art will appreciate that the illustrated element boundaries (e.g., boxes, groups of boxes, or other shapes) in the figures represent one example of the boundaries. It may be that in some examples, one element may be designed as multiple elements or that multiple elements may be designed as one element. In some examples, an element shown as an internal component of one element may be implemented as an external component in another, and vice versa. Furthermore, elements may not be drawn to scale.

Various embodiments will hereinafter be described in accordance with the appended drawings, which are provided to illustrate, and not limit, the scope in any manner, wherein similar designations denote similar elements, and in which:

FIGS. 5A, 5B, 5C, 5D, 5E, and 5F are example user-interfaces that may be presented to a user on a display device of a computing device for receiving one or more parameters associated with a human subject, in accordance with at least one embodiment.

FIG. 7 shows an example equation (1).

DETAILED DESCRIPTION

Figure 1:
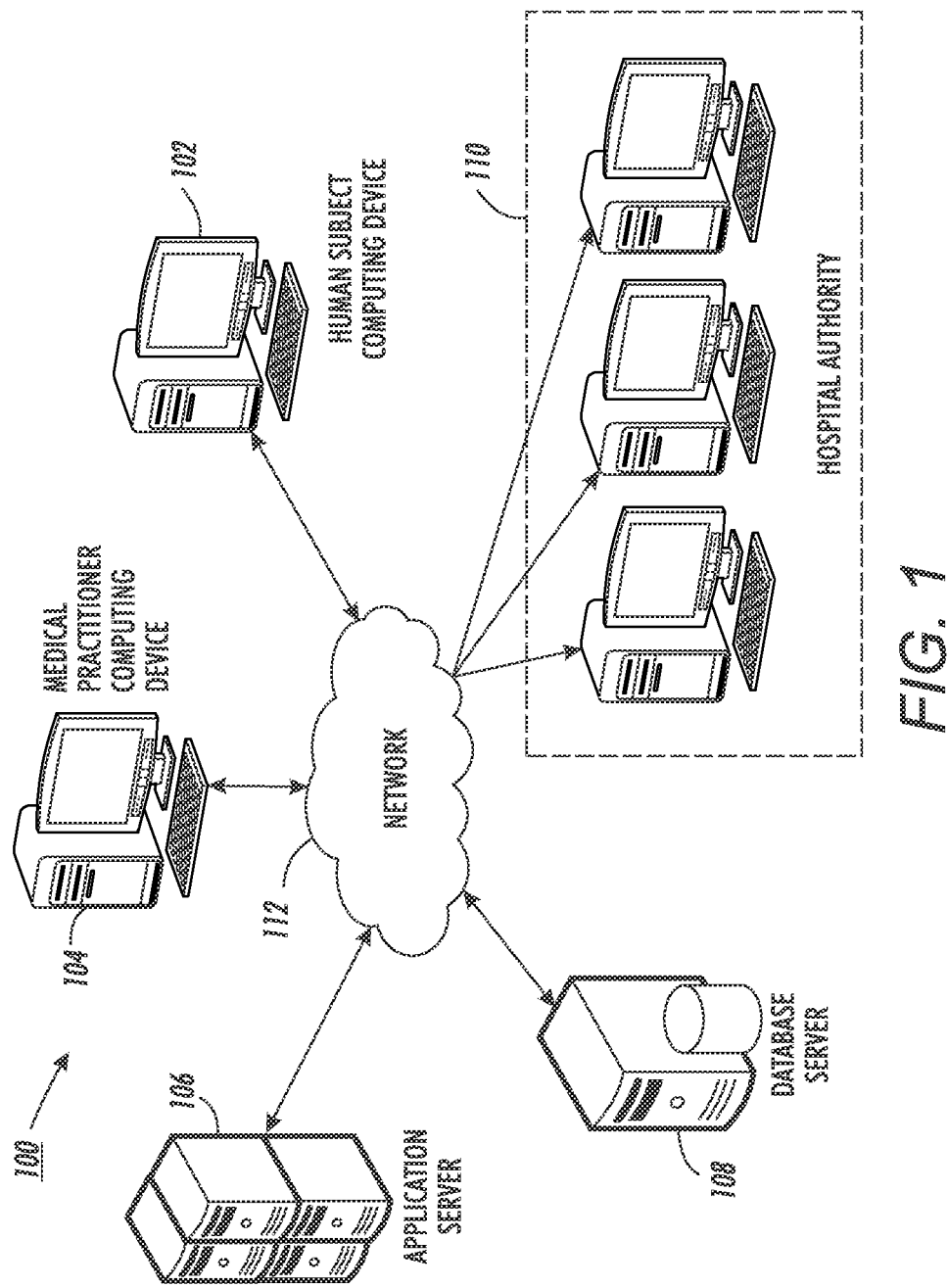
FIG. 1 illustrates a system environment diagram, in which various embodiments may be implemented.

The present disclosure is best understood with reference to the detailed figures and descriptions set forth herein. Various embodiments are discussed below with reference to the figures. However, those skilled in the art will readily appreciate that the detailed descriptions given herein with respect to the figures are simply for explanatory purposes, as the methods and systems may extend beyond the described embodiments. For example, the teachings presented and the needs of a particular application may yield multiple alternate and suitable approaches to implement the functionality of any detail described herein. Therefore, any approach may extend beyond the particular implementation choices in the following embodiments described and shown.

References to "one embodiment," "at least one embodiment," "an embodiment," "one example", "an example", "for example" and so on, indicate that the embodiment(s) or example(s) so described may include a particular feature, structure, characteristic, property, element, or limitation, but that not every embodiment or example necessarily includes that particular feature, structure, characteristic, property, element, or limitation. Furthermore, repeated use of the phrase "in an embodiment" does not necessarily refer to the same embodiment.

"Human subject" corresponds to a human being, who may be suffering from a health condition or a disease. In an embodiment, the human subject may correspond to a person who seeks a medical opinion on his/her health condition.

A "patient dataset" corresponds to historical data pertaining to one or more human subjects previously admitted to a medical institution or taking medical consultation from the medical institution. In an embodiment, the patient dataset includes information pertaining to measured one or more physiological parameters. In addition, the patient dataset may further include other clinical and non-clinical data associated with the one or more human subjects such as demographic data, past diseases, past medications, past addictions, etc. Hereinafter, the term "patient dataset" has been interchangeably referred as "medical record data".

"Patients" refer to one or more human subjects who may receive medical treatment for an ailment/health condition. In an embodiment, prior to receiving the medical treatment, one or more physiological parameters associated with the patients may be measured. Based on the measured one or more physiological parameters, the other clinical data, and the non-clinical data associated with the patients, a health condition of the patients may be determined.

"One or more parameters associated with a human subject" refer to clinical and non-clinical features associated with a human subject. In an embodiment, the one or more parameters associated with the human subject may have an associated data type. Examples of the data type may include, but are not limited to, a binary data type (e.g., gender, parameters related to past addictions, past diseases, past medications, etc.), a categorical data type (e.g., education level, job type, parameters related to radiological results, etc.), and a numerical data type (e.g., age, parameters related to blood investigation results, etc.).

A "data view" refers to a data structure that may include data of human subjects across a set of parameters of a similar data type or logical context. In an embodiment, the data view may correspond to a matrix with rows corresponding to the one or more human subjects and columns corresponding to the set of parameters from the one or more parameters. Examples of data views include, but are not limited to, a demographic data view, a past diseases data view, a past addictions data view, a blood investigations data view, a radiological investigations data view, and a past medications data view. Further, the data view may be realized through various data structures such as, but not limited to, an array, a record, a hash table, a union, a graph, and a linked list.

"One or more categories" correspond to classes in which one or more patients are categorized. In an embodiment, each of the one or more classes is representative of a range of a health condition scores. In an embodiment, the patients are categorized in the one or more categories based on the measured one or more physiological parameters. In an embodiment, a category in which a patient has been categorized may be deterministic of at least treatment plan of the patient.

A "treatment plan" refers to a decision taken for administering a treatment course to a patient by a medial institution or a medical practitioner. In an embodiment, the treatment plan may include a prescription of one or more medicines and/or a recommendation of one or more clinical tests at pre-determined intervals to the patient. In an embodiment, the treatment plan of a patient may be determined based on the health condition of the patient.

A "stroke score" refers to a score assigned to a human subject that is deterministic of a severity of stroke. In an embodiment, the stroke score is determined based on a measure of one or more physiological parameters. The stroke score may also be determined based on the clinical and the non-clinical data associated with the human subject. In an embodiment, the stroke score is in accordance to a National Institute of Health Stroke Scale (NIHSS) score.

"Health condition score" refers to a score assigned to a human subject that is indicative of a severity of a disease or health condition. In an embodiment, the health condition score is determined based on the one or more physiological parameters.

"Classifier" refers to a mathematical model that may be configured to categorize a human subject in one of one or more categories. In an embodiment, the classifier is trained based on historical data. Examples of the one or more techniques that may be utilized to train a classifier include, but are not limited to, a Support Vector Machine (SVM), a Logistic Regression, a Bayesian Classifier, a Decision Tree Classifier, a Copula-based Classifier, a K-Nearest Neighbors (KNN) Classifier, or a Random Forest (RF) Classifier.

FIG. 1 illustrates a system environment 100, in which various embodiments may be implemented. The system environment 100 includes a human subject computing device 102, a medical practitioner computing device 104, an application server 106, a database server 108, a hospital authority 110, and a network 112.

The human subject computing device 102 corresponds to a computing device that is operable by a human subject. In an embodiment, the human subject computing device 102 may have one or more coupled sensors, which may be either built into the human subject computing device 102 or connected to it. The one or more sensors enable the human subject to measure one or more physiological parameters associated with him/her In addition, the human subject computing device 102 may store clinical and non-clinical data associated with the human subject. Examples of the clinical data include, but are not limited to, blood investigations, past diseases, past addictions, past medications, radiological investigations, and so forth. Examples of non-clinical data include demographic data associated with the human subject such as, but not limited to, age, gender, education level, type of job, and so forth. The measurements of the one or more physiological parameters, the clinical data, and the non-clinical data are collectively hereinafter referred as one or more parameters associated with the human subject. In an embodiment, the human subject computing device 102 may transmit the one or more parameters (i.e., the one or more physiological parameters, other clinical data and the non-clinical data) associated with the human subject to the application server 106. FIGS. 5A through 5F illustrate examples of user-interfaces that may be presented on the human subject computing device 102 to receive the one or more parameters associated with the human subject from the human subject. In an embodiment, the human subject computing device 102 may receive a health condition score of the human subject from the application server 106. FIG. 6 illustrates an example user-interface that may be presented on the human subject computing device 102 to display the health condition score of the human subject.

In another embodiment, the human subject may visit a laboratory that may have the one or more sensors to measure the one or more physiological parameters. The human subject may provide the other clinical data and the non-clinical data during the laboratory visit. Thereafter, a computing device at the laboratory may transmit the one or more parameters (i.e., the one or more physiological parameters, other clinical data and the non-clinical data) associated with the human subject to the application server 106.

In an embodiment, the human subject computing device 102 may be realized using any computing device such as a desktop, a laptop, a personal digital assistant (PDA), a tablet computer, and the like.

The medical practitioner computing device 104 corresponds to a computing device that is operable by the medical practitioner. In an embodiment, the medical practitioner computing device 104 may have the one or more coupled sensors. Such sensors are utilizable to measure the one or more physiological parameters associated with the human subject. In addition, the medical practitioner may receive the clinical data and the non-clinical data associated with the human subject from the human subject. The medical practitioner computing device 104 may then store the one or more physiological parameters, the clinical data, and the non-clinical data associated with the human subject (collectively referred as the one or more parameters), which the medical practitioner computing device 104 may transmit to the application server 106. FIGS. 5A through 5F illustrate examples of user-interfaces that may be presented on the medical practitioner computing device 104 to receive the one or more parameters associated with the human subject from the medical practitioner. In an embodiment, the medical practitioner computing device 104 may receive a health condition score from the application server 106. FIG. 6 illustrates an example user-interface that may be presented on the medical practitioner computing device 104 to display the health condition score of the human subject to the medical practitioner. Based on the health condition score, the medical practitioner may determine a further course of action. Further, the medical practitioner computing device 104 may query the database server 108 to extract/update a medical record data (which includes the one or more parameters) associated with the human subject.

In an embodiment, the medical practitioner computing device 104 may be realized using any computing device such as a desktop, a laptop, a personal digital assistant (PDA), a tablet computer, and the like.

The application server 106 is configured to categorize the one or more parameters associated with one or more human subjects into one or more data views. In an embodiment, each of the one or more data views may correspond to a first data structure for storing a set of parameters from the one or more parameters. In an embodiment, the categorization of the one or more parameters is based on a data type associated with each of the one or more parameters. Examples of the data types include, but are not limited to, a categorical data type, a binary data type, or a numerical data type. Further, the application server 106 may transform the one or more data views into a second data structure. In an embodiment, the second data structure may be representative of the set of parameters across the one or more data views. Post transforming the one or more data views into the second data structure, the application server 106 trains a classifier based on the second data structure. In an embodiment, the application server 106 may utilize the classifier to categorize the one or more human subjects into one or more categories each of which may be indicative of a health condition score of the one or more human subjects. In an embodiment, the application server 106 may present a user interface on the medical practitioner computing device 104 through which the health conditions score of the human subject is displayed to the medical practitioner. An embodiment of a method for training a classifier for categorizing one or more human subjects in one or more categories has been explained further in conjunction with FIG. 3.

In an embodiment, the application server 106 may be realized through various types of servers such as, but not limited to, Java server, .NET framework, and Base4 server.

A person with ordinary skills in the art would understand that scope of the disclosure is not limited to having the application server 106 as a separate entity. In an embodiment, the application server 106 may be embedded in the medical practitioner computing device 104 as a software application.

In an embodiment, the database server 108 is configured to store the medical record data. In an embodiment, the medical record data may include information pertaining to the one or more parameters associated with each of the one or more human subjects. In an embodiment, the database server 108 may receive a query from the application server 106, one or more computing devices of the hospital authority 110, and/or the medical practitioner computing device 104 to extract/update the medical record data associated with the one or more human subjects. For example, the medical practitioner computing device 104 may store one or more parameters associated with a human subject on the database server 108. The application server 106 may query the database server 108 for extracting records pertaining to the one or more human subjects, where each record includes the one or more parameters of the respective human subject. The application server 106 may utilize the extracted records for training the classifier for predicting a health condition score of the one or more human subjects. The database server 108 may be realized through various technologies such as, but not limited to, Microsoft® SQL server, Oracle, and My SQL. In an embodiment, the medical practitioner computing device 104, the one or more computing devices of the hospital authority 110, and/or the application server 106 may connect to the database server 108 using one or more protocols such as, but not limited to, Open Database Connectivity (ODBC) protocol and Java Database Connectivity (JDBC) protocol.

A person with ordinary skills in the art would understand that scope of the disclosure is not limited to having the database server 108 as a separate entity. In an embodiment, the database server 108 may be embedded along with application server 106.

The hospital authority 110 corresponds to a hospital infrastructure that includes at least one computing device. The computing device in the hospital authority 110 receives the health condition score associated with the human subject from the application server 106. Based on the health condition score, the computing device in the hospital authority may inform one or more departments in the hospital authority 110 to make preparations for disposition of the human subject in accordance with the health condition score associated with the human subject. FIG. 6 illustrates an example user-interface that may be presented on the at least one computing of the hospital authority 110 to display the health condition score of the human subject.

A person skilled in the art would appreciate that the one or more parameters of the human subject may also be provided through the at least one computing device of the hospital authority 110. For example, during consultation or admission of a human subject in the hospital, the one or more parameters of the human subject may be provided through the at least one computing device of the hospital authority 110. FIGS. 5A through 5F illustrate examples of user-interfaces that may be presented on the at least one computing device of the hospital authority 110 to receive the one or more parameters associated with the human subject.

The network 112 corresponds to a medium through which content and messages flow between various devices of the system environment 100 (e.g., the human subject computing device 102, the medical practitioner computing device 104, the application server 106, the database server 108, and the one or more computing devices of the hospital authority 110). Examples of the network 112 may include, but are not limited to, a Wireless Fidelity (Wi-Fi) network, a Wireless Area Network (WAN), a Local Area Network (LAN), or a Metropolitan Area Network (MAN). Various devices in the system environment 100 can connect to the network 112 in accordance with various wired and wireless communication protocols such as Transmission Control Protocol and Internet Protocol (TCP/IP), User Datagram Protocol (UDP), and 2G, 3G, or 4G communication protocols.

Figure 2:
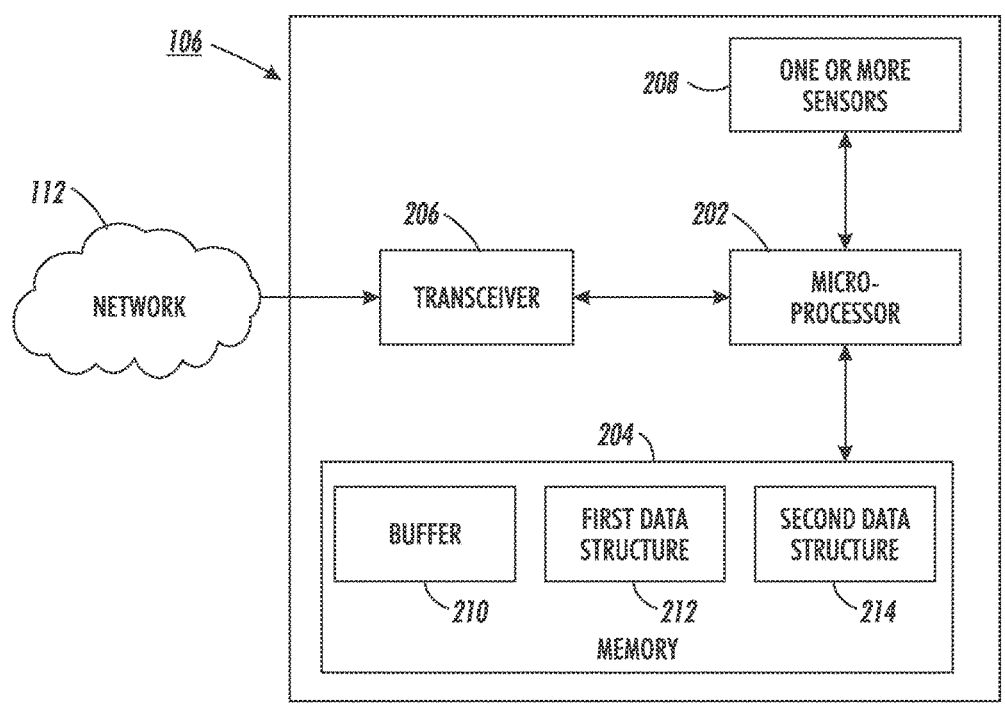
FIG. 2 is a block diagram of an application server, in accordance with at least one embodiment.

FIG. 2 is a block diagram of the application server 106, in accordance with at least one embodiment. The application server 106 includes a micro-processor 202, a memory 204, and a transceiver 206. The application server 106 may further include one or more sensors 208 coupled to the micro-processor 202.

The micro-processor 202 is coupled to the memory 204 and the transceiver 206. The micro-processor 202 includes suitable logic, circuitry, and/or interfaces that are operable to execute one or more instructions stored in the memory 204 to perform predetermined operation. The memory 204 may be operable to store the one or more instructions. The micro-processor 202 may be implemented using one or more processor technologies known in the art. Examples of the micro-processor 202 include, but are not limited to, an X86 processor, a RISC processor, an ASIC processor, a CISC processor, or any other processor.

The memory 204 stores a set of instructions and data. In an embodiment, the memory 204 may include a buffer 210, a first data structure 212, and a second data structure 214. Some of the commonly known memory implementations include, but are not limited to, a random access memory (RAM), a read only memory (ROM), a hard disk drive (HDD), and a secure digital (SD) card. Further, the memory 204 includes the one or more instructions that are executable by the micro-processor 202 to perform specific operations. It will be apparent to a person having ordinary skills in the art that the one or more instructions stored in the memory 204 enables the hardware of the application server 106 to perform the predetermined operation.

The transceiver 206 transmits and receives messages and data to/from various devices of the system environment 100 (e.g., the human subject computing device 102, the medical practitioner computing device 104, the database server 108, and the one or more computing devices of the hospital authority 110). In an embodiment, the transceiver 206 may be realized through, but not limited to, an antenna, an Ethernet port, a USB port or any other port that can be configured to receive and transmit data. The transceiver 206 transmits and receives data/messages in accordance with the various communication protocols, such as, TCP/IP, UDP, and 2G, 3G, or 4G communication protocols.

The one or more sensors 208 are configured to measure one or more physiological parameters associated with a human subject. Examples of the one or more sensors 208 include, but are not limited to, blood sugar sensor, breath carbon dioxide concentration sensor, breath oxygen concentration sensor, blood pressure sensor, heart rate sensor, body temperature sensor, and the like.

Figure 3:
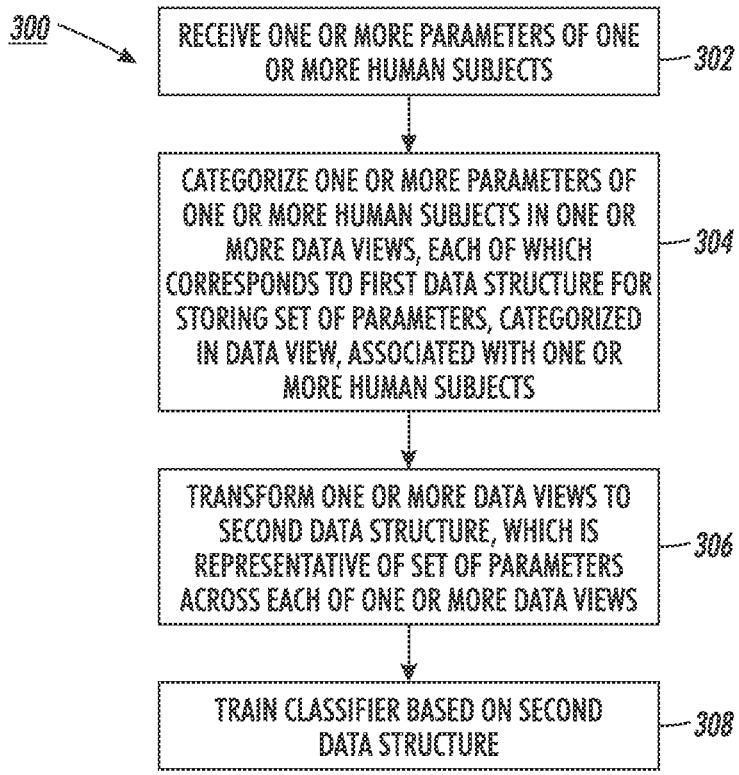
FIG. 3 is a flowchart illustrating a method for training a classifier for categorizing one or more human subjects in one or more categories, in accordance with at least one embodiment.

The operation of the application server 106 for training a classifier has been described in conjunction with FIG. 3.

FIG. 3 is a flowchart 300 illustrating a method for training a classifier for categorizing the one or more human subjects in one or more categories, in accordance with at least one embodiment. The flow chart 300 has been described in conjunction with FIG. 1 and FIG. 2.

At step 302, the one or more parameters of the one or more human subjects are received. In an embodiment, the micro-processor 202 receives the one or more parameters of the one or more human subjects from the database server 108 through the transceiver 206.

At step 304, the one or more parameters of the one or more human subjects are categorized in the one or more data views. In an embodiment, the micro-processor 202 is configured to categorize the one or more parameters in the one or more data views. In an embodiment, each of the one or more data views may correspond to the first data structure 212 for storing the set of parameters that has been categorized in the data view. In an embodiment, the micro-processor 202 may store each data view as a respective first data structure 212 in the memory 204. In an embodiment, the categorization of the one or more parameters may be based on the data type of each of the one or more parameters. Examples of the data types may include, but are not limited to, a categorical data type, a binary data type, or a numerical data type. In another embodiment, the set of parameters categorized within each of the one or more data views may be similar to one another in a logical context. In an embodiment, the various logical contexts, based on which the one or more parameters are to be categorized in the one or more data views, may be provided by a user. Alternatively, the logical contexts may be determined by the micro-processor 202 heuristically. For example, parameters related to past diseases suffered by the human subjects (a logical context) may be clubbed together in a past diseases data view. Similarly, parameters related to past medications prescribed to the human subjects (another logical context) may be put together in a past medications data view. In another embodiment, the micro-processor 202 may categorize the one or more parameters based on both, the data types associated with the one or more parameters, and the logical context. Examples of the one or more data views may include, but are not limited to, a demographic data view, a past diseases data view, a past addictions data view, a blood investigations data view, a radiological investigations data view, or a past medications data view.

Further, for each of the one or more human subjects, the one or more parameters may further include a health condition score (that was previously determined for each of the one or more human subjects). In an embodiment, the micro-processor 202 may create a data view for the health condition score. The following table illustrates an example of the set of parameters from the one or more parameters categorized in each of the one or more data views:

TABLE 1

Example of the one or more data views and respective set of parameters categorized in each of the one or more data views
Data views and set of respective parameters

| Demographic Data View | Past Diseases Data View | Past Addictions Data View | Blood Investigations Data View | Radiological Investigations Data View | Past Medications Data View |
|---|---|---|---|---|---|
| Age | Past Occurrence of Hypertension | Smoking Addiction | Total Blood Count | Echo Scan | Aspirin Intake |
| Gender | Past Occurrence of Diabetes Mellitus | Alcohol Addiction | Hemoglobin Count | MRI Scan | Clopidogrel Intake |
| Education Level | Past Occurrence of Heart Disease | Tobacco Addiction | RBS Count | CT Scan | Statins Intake |
| Job Type | Past Occurrence of Cerebrovascular accident | | Blood Platelets Count | | CCB Intake |
| | | | Creatinine Count | | ACEI Intake |
| | | | Serum Sodium Count | | Anti-Epileptics Intake |
| | | | Blood Albumin Count | | Anti-Diabetics Intake |

As illustrated in Table 1, the one or more data views may include parameters of heterogeneous data types. For instance, the Demographic data view includes parameters such as age, gender, education level, and job type. The parameter "age" is of numerical data type and the parameter "gender" is of binary data type. Further, the parameters "education level" and "job type" are of categorical data types. However, other data views, such as the Past Diseases data view, the Past Addiction data view, the Blood Investigations data view, the Radiological Investigations data view, and the Past Medications data view, all include parameters of homogenous data types. For instance, all the parameters categorized in the Past Diseases data view, the Past Addictions data view, and the Past Medications data view are of binary data type (i.e., such parameters may have only yes/no type of values). Further, all the parameters categorized in the Blood Investigations data view are of numerical data type, while all the parameters categorized in the Radiological Investigations data view are of categorical data type.

In an embodiment, the first data structure 212 associated with each data view may correspond to a matrix for storing data pertaining to the one or more human subjects across the set of parameters (in the respective data view). Each column in the matrix may correspond to an individual parameter from the set of parameters, while each row may correspond to an individual human subject from the one or more human subjects. For instance, the first data structure 212 associated with the Demographic data view may correspond to a matrix that includes 4 columns (age, gender, education level, and job type), one for each parameter categorized in the Demographic data view. The number of rows of the matrix may correspond to the number of human subjects in the medical record data, one row per human subject.

At step 306, the one or more data views are transformed into the second data structure 214. In an embodiment, the micro-processor 202 is configured to transform the one or more data views into the second data structure 214. In an embodiment, the micro-processor 202 may store the transformation of the one or more data views as the second data structure 214 in the memory 204. To perform the transformation, in an embodiment, the micro-processor 202 may utilize one or more multi-view learning techniques such as, but not limited to, a Collective Matrix Factorization (CMF) technique, a Principal Component Analysis (PCA) technique, a Non-negative Matrix Factorization (NMF) technique, a Canonical Correlation Analysis technique (CCA), or an Inter-Battery Factor Analysis (IBFA) technique. In an embodiment, the second data structure 214 may be representative of the set of parameters across each of the one or more data views.

For example, considering a scenario where the micro-processor 202 utilizes the Collective Matrix Factorization (CMF) technique to transform the one or more data views into the second data structure 214. As already explained, the first data structure 212 associated with each of the one or more data views may correspond to a matrix with the columns as the set of parameters categorized in that data view and the rows as the one or more human subjects. In an embodiment, the one or more human subjects (stored as rows in each of the one or more data views), and the set of parameters (stored as the columns) for each data view corresponds to an entity set. For example, for the blood investigations data view, the one or more human subjects may correspond to a first entity set. Further, the set of parameters (such as hemoglobin count, RBC count) may correspond to second entity set. Similarly, for each data view, the set of parameters correspond to a respective entity set.

FIG. 7 shows an example equation (1) illustrating transformation between data view matrices. For example, there are three matrices X1, X2, and X3, corresponding to three data views, e.g., the blood investigations data view, the past medications data view, and the demographic data view. The matrices X1, X2, and X3 have m rows each and c1, c2, and c3 columns respectively. Hence, for the one or more data views, there exist four entity sets (human subject entity set, demographic entity set, past medication entity set, and blood investigation entity set). Considering that $e_i$ represents entity sets for the one or more data views. For instance, the matrix X1 may represent the blood investigations data view with an entity set e1 (m rows) representing the set of the one or more human subjects and an entity set e2 (c1 columns) representing the set of parameters categorized in the blood investigations data view (such as total blood count, hemoglobin count, a RBS count, a blood platelet count, a creatinine count, a serum sodium count, a blood albumin count, and so forth). The matrix X1 may then represent a relationship between the entity sets e1 and e2. Similarly, the matrix X2 may represent the past medications data view as a relationship between the entity set e1 (m rows) and an entity set e3 (c2 columns), where the entity set e3 may represent the set of parameters categorized in the past medications data view. Further, the matrix X3 (for the demographic data view) may be representative of a relationship between the entity set e1 (m rows) and an entity set e4 (c3 columns), where the entity set e4 may represent the set of parameters categorized in the demographic data view. The three data views (i.e., the matrices X1, X2, and X3) may be transformed into a larger matrix (collective matrix) Y as represented in equation (1) shown in FIG. 7, where, $X_i^T$: transpose of the matrix $X_i$, ?: missing/blank values (may be padded with zeroes), and Y: collective matrix of the one or more data views.

As illustrated in equation (1) shown in FIG. 7, the data views represented by matrices X1, X2, and X3 are combined into the collective matrix Y. The collective matrix Y may be a square matrix of the dimensions (e1+e2+e3+e4)*(e1+e2+e3+e4). The micro-processor 202 may factorize the collective matrix Y into low-rank matrices is represented in example equation (2) shown in FIG. 8.

Figure 8:
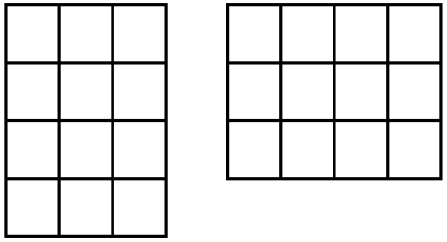
FIG. 8 shows an example equation (2).

As illustrated in equation (2) shown in FIG. 8, the collective matrix Y is factorized into two matrices U and $U^T$. In an embodiment, the micro-processor 202 may utilize a Bayesian learning technique to perform the decomposition/factorization such that the matrix U is of 'k' dimensions across the entity set e1 (i.e., the data set of the one or more human subjects). In embodiment, the matrix U may correspond to the second data structure 214, which is a joint representation of all data views (e.g., X1, X2, and X3) for the entity set e1. In an embodiment, within the second data structure 214, common/correlated information among the one or more data views may be preserved, while data view specific information (i.e., information present only in a particular data view, which is not correlated to information present in other data views) may be discarded. For example, the parameters age and gender of the demographic data view may be correlated to the other parameters of the other data views. Hence, information pertaining to the age and the gender of the one or more human subjects may be preserved within the second data structure 214. However, the parameters education and job level of the demographic data view may not as such be correlated (or may be weakly correlated) to the other parameters of the other data views. Therefore, information pertaining to the education and the job level of the one or more human subjects may be omitted from the second data structure 214.

In an embodiment, the micro-processor 202 may combine the one or more data views into the collective matrix Y and store the collective matrix Y within the buffer 210 in the memory 204. During the factorization of the collective matrix Y into the transformed second data structure 214, the collective matrix Y may be stored within the buffer 210. When the collective matrix Y is transformed (i.e., converted into the lower rank matrices U and $U^T$), the micro-processor 202 stores the transformed matrix as the second data structure 214 within the memory 204.

In an embodiment, the dimension 'k' of the matrix U may be a controllable parameter that may be adjusted by cross-validation. The adjustment of the dimension 'k' has been explained in step 308.

By utilizing a Bayesian learning technique for Collective Matrix Factorization, data of numerical data type may be obtained within the factorized/decomposed matrix, irrespective of the initial data type of data within the individual data views. Such numerical data may be suitable for further analysis and training of a classifier using any known technique in the art. Further, missing values within the individual data views may be imputed during the transformation process. This may lead to an improvement of the prediction accuracy of classifiers trained on such data. Further, no parameter tuning may be required for Bayesian learning.

At step 308, a classifier is trained on the second data structure 214. In an embodiment, the micro-processor 202 is configured to train the classifier on the second data structure 214. In an embodiment, the classifier may be training by utilizing one or more machine learning techniques such as, but not limited to, a Support Vector Machine (SVM), a Logistic Regression, a Bayesian Classifier, a Decision Tree Classifier, a Copula-based Classifier, a K-Nearest Neighbors (KNN) Classifier, or a Random Forest (RF) Classifier. As discussed above, the micro-processor 202 creates a data view for the health condition score, which includes predetermined values of the health condition score of each of the one or more human subjects. In an embodiment, the micro-processor 202 may utilize the health condition score data view to train the classifier on the second data structure 214. Thus, the classifier may be trained to categorize the one or more human subjects into one or more categories, each of which is indicative of a range of the health condition score of the one or more human subjects. For example, the health condition score may correspond to an NIHSS score. In such a scenario, the range of the NIHSS score, so obtained, may be utilized to predict a severity of stroke among the one or more human subjects. The classification of the one or more human subjects into the one or more categories by utilizing the classifier has been further explained in FIG. 4.

Adjustment of the Dimension 'k' of the Second Data Structure

In an embodiment, the micro-processor 202 may utilize a leave-one out cross validation technique to train a classifier based on a training dataset of human subjects for whom the health condition score range is known. Thus, one of the data views of the training dataset of human subjects may include a health condition score data view that includes predetermined values of the health condition scores of each of the one or more human subjects. The training dataset may be categorized into one or more data views (refer step 304) and thereafter transformed into the second data structure 214 (refer step 306) with an empirically/heuristically selected value of 'k'. For each observation in the second data structure 214, the micro-processor 202 may train the classifier on the remaining observations and use the classifier to predict the health condition score range of the observation left-out. Thereafter, the micro-processor 202 may determine a classification accuracy of the classifier based on proportions of predictions that are correct. Further, the micro-processor 202 may empirically/heuristically select a second value of 'k'. Thereafter, the micro-processor 202 may re-transform the one or more data views into the second data structure 214 with the second value of 'k' as its dimension. A new classifier may be similarly trained on the second data structure 214 and the classification accuracy may be determined for the new classifier. The micro-processor 202 may select that value of 'k' that yields a higher classification accuracy for the Bayesian learning based CMF transformation of the actual dataset of the one or more human subjects, for whom the health condition score range is to be estimated. A person skilled in the art would appreciate that the process of selecting newer values of k may be repeated until a pre-determined classification accuracy or a pre-determined value of k is reached.

Figure 4:
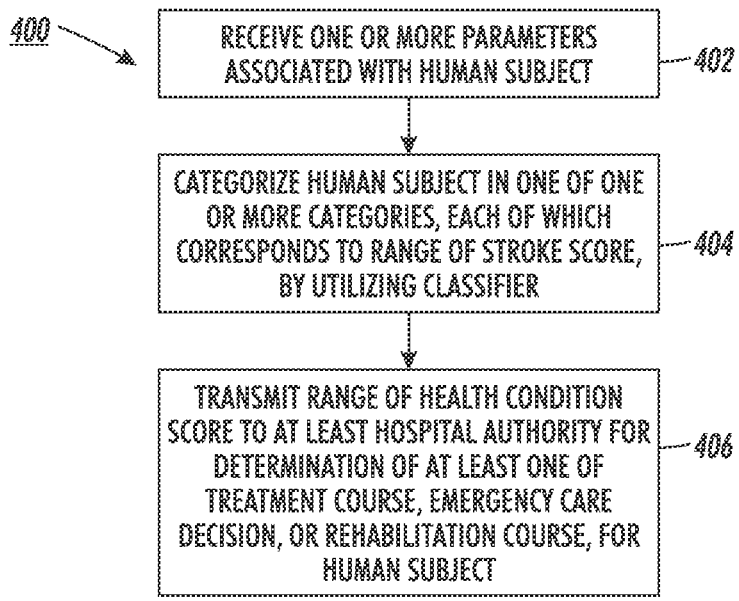
FIG. 4 is a flowchart illustrating a method for determining a stroke score of a human subject, in accordance with at least one embodiment.

FIG. 4 is a flowchart 400 illustrating a method for determining a health condition score of a human subject, in accordance with at least one embodiment.

At step 402, the one or more parameters associated with a human subject are received. In an embodiment, the micro-processor 202 is configured to receive the one or more parameters including the measure of the one or more physiological parameters, other clinical data, and non-clinical data, associated with the human subject from at least one of the human subject computing device 102, the medical practitioner computing device 104, or the computing device of the hospital authority 110. FIGS. 5A through 5F illustrate examples of user-interfaces that may be presented on the human subject computing device 102, the medical practitioner computing device 104, and/or the computing device of the hospital authority 110 to receive the one or more parameters associated with the human subject.

Prior to receiving the measure of the one or more physiological parameters, the medical practitioner may examine the human subject. The examination of the human subject may include measuring the one or more physiological parameters using one or more sensors or blood work tests (e.g., a biosensor). Post determining the one or more physiological parameters, the medical practitioner may input the measured one or more physiological parameters, the other clinical data, and the non-clinical data through the user interface of the medical practitioner computing device 104.

A person with ordinary skills in the art would understand that the scope of the disclosure is not limited to measuring the one or more physiological parameters by the medical practitioner. In an embodiment, the human subject may own the one or more sensors through which the human subject may himself/herself measure the one or more physiological parameters. Further, in an embodiment, the human subject may get the one or more physiological parameters measured from a pathological laboratory. In both these scenarios, the human subject may provide the one or more parameters associated with himself/herself through the human subject computing device 102. Further, in an embodiment, the one or more sensors 208 in the application server 106 may measure the one or more physiological parameters associated with the human subject without departing from the scope of the disclosure.

At step 404, the human subject is categorized in one of the one or more categories based on the classifier. In an embodiment, the micro-processor 202 is configured to classify the human subject into one of the one or more categories indicative of a range of a health condition score by utilizing the classifier trained at step 308.

At step 406, the range of the health condition score is transmitted to the one or more computing devices of the hospital authority 110. Further, the health condition score may also be transmitted to the medical practitioner computing device 104. In an embodiment, the micro-processor 202 is configured to transmit the range of the health condition score to the one or more computing devices of the hospital authority 110 or the medical practitioner computing device 104. In addition, in an embodiment, the micro-processor 202 may also transmit the range of the health condition score of the human subject to the human subject computing device 102. FIG. 6 illustrates an example user-interface that may be presented a computing device (e.g., the human subject computing device 102, the medical practitioner computing device 104, the computing device of the hospital authority 110, etc.) to display the health condition score of the human subject.

For example, the health condition score may correspond to a stroke score such as an NIHSS score. In an embodiment, the category in which an individual is classified is representative of the range of the stroke score. For example, the human subject may be categorized in one of the four categories, as depicted in the table below:

TABLE 2

Example of the categories of the NIHSS score ranges

| Categories | NIHSS score |
| --- | --- |
| Category-1 | 0-10 |
| Category-2 | 11-20 |
| Category-3 | 21-30 |
| Category-4 | 31-42 |

For instance, if the human subject is categorized in the category-2, the human subject has a NIHSS score within the range of 11-20. A person skilled in the art would appreciate that the scope of the disclosure is not limited to the examples of the categories of the NIHSS score ranges as provided in Table 2. The NIHSS score ranges may be segregated in other ways without departing from the spirit of the disclosure.

The medical practitioner may determine a severity of the stroke based on the category in which the human subject has been categorized. In an embodiment, the following table illustrates the severity of the stroke versus the one or more categories:

TABLE 3

| Severity of the stroke | |
| --- | --- |
| Stroke score range | Stroke severity |
| 0-10 | Minor stroke |
| 11-20 | Moderate stroke |
| 21-30 | Moderate to severe stroke |
| 31-42 | Severe stroke |

For example, if the human subject has been categorized in the category-2, i.e., the stroke score range of the human subject is 11 to 20 (refer Table 2), the stroke severity risk is moderate (refer Table 3). Based on the severity of the stroke, the medical practitioner may plan the treatment of the human subject. For example, the medical practitioner may determine the dosage of the tPA medicine based on the severity of the stroke. Further, the medical practitioner may suggest admission of the human subject in the hospital based on the categorization.

The stroke score may be utilized by the hospital authorities to determine the type of care required by the human subject. The following table illustrates example actions that the hospital may have to take on receiving the stroke score:

TABLE 4

| Stroke score versus hospital disposition | |
| --- | --- |
| Stroke score | Hospital Disposition |
| <=5 | Around 80% discharged home |
| 6-13 | Acute in-patient rehabilitation required |
| >=14 | Long term care in nursing facility |

In an embodiment, the care provided by the hospital authority may include, but is not limited to, a treatment course for the human subject, an emergency care decision associated with the human subject, or a rehabilitation course for the human subject.

A person with ordinary skills in the art would understand that the scope of the disclosure is not limited to determining the stroke score for the human subject. In an embodiment, the disclosure may be implemented for determining scores pertaining to various other health conditions such as Framingham risk score, and coronary heart disease risk score.

FIGS. 5A, 5B, 5C, 5D, 5E, and 5F are example user-interfaces that may be presented to a user on a display device of a computing device for receiving one or more parameters associated with a human subject, in accordance with at least one embodiment. FIG. 6 is an example user-interface that may be presented to the user on the display device the computing device to display a classification of the human subject in one or more categories indicative of a health condition of the human subject, in accordance with at least one embodiment.

A person skilled in the art would appreciate that the user may correspond to a medical practitioner, an individual associated with the hospital authority, and/or the human subject himself/herself. Accordingly, the computing device on which the respective user-interfaces of FIGS. 5A-5F and FIG. 6 are presented may correspond to the medical practitioner computing device 104, a computing device of the hospital authority 110, and/or the human subject computing device 102.

Figure 5A:
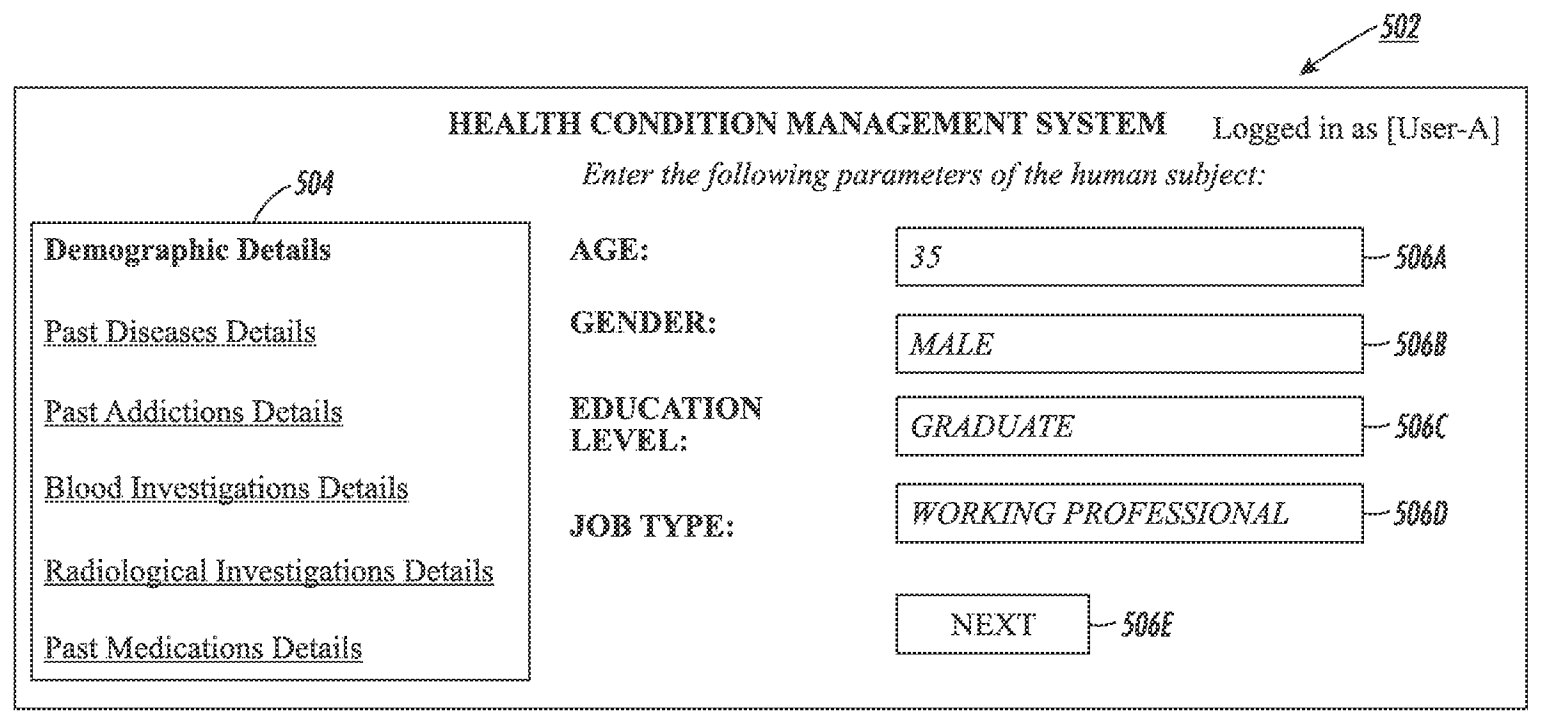
Figure 5B:
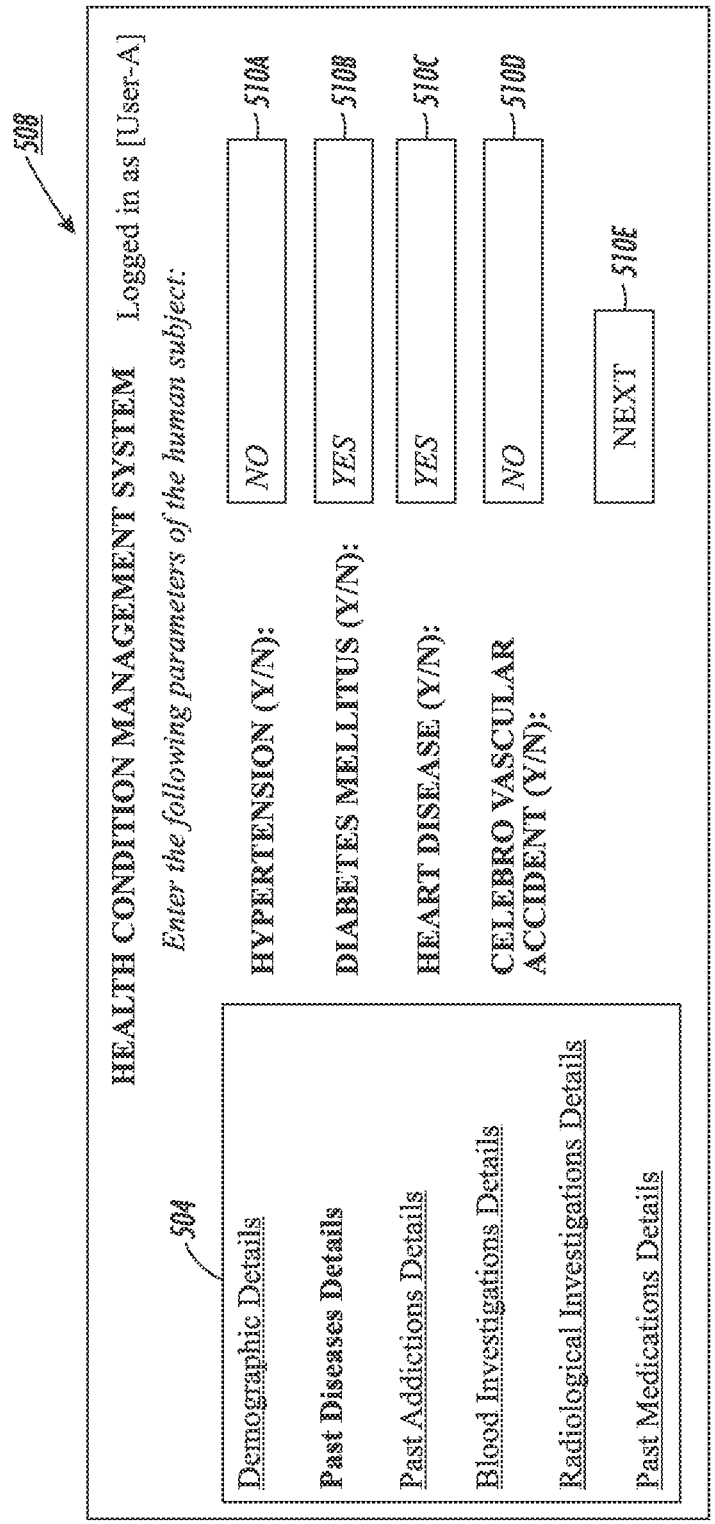
Figure 6:
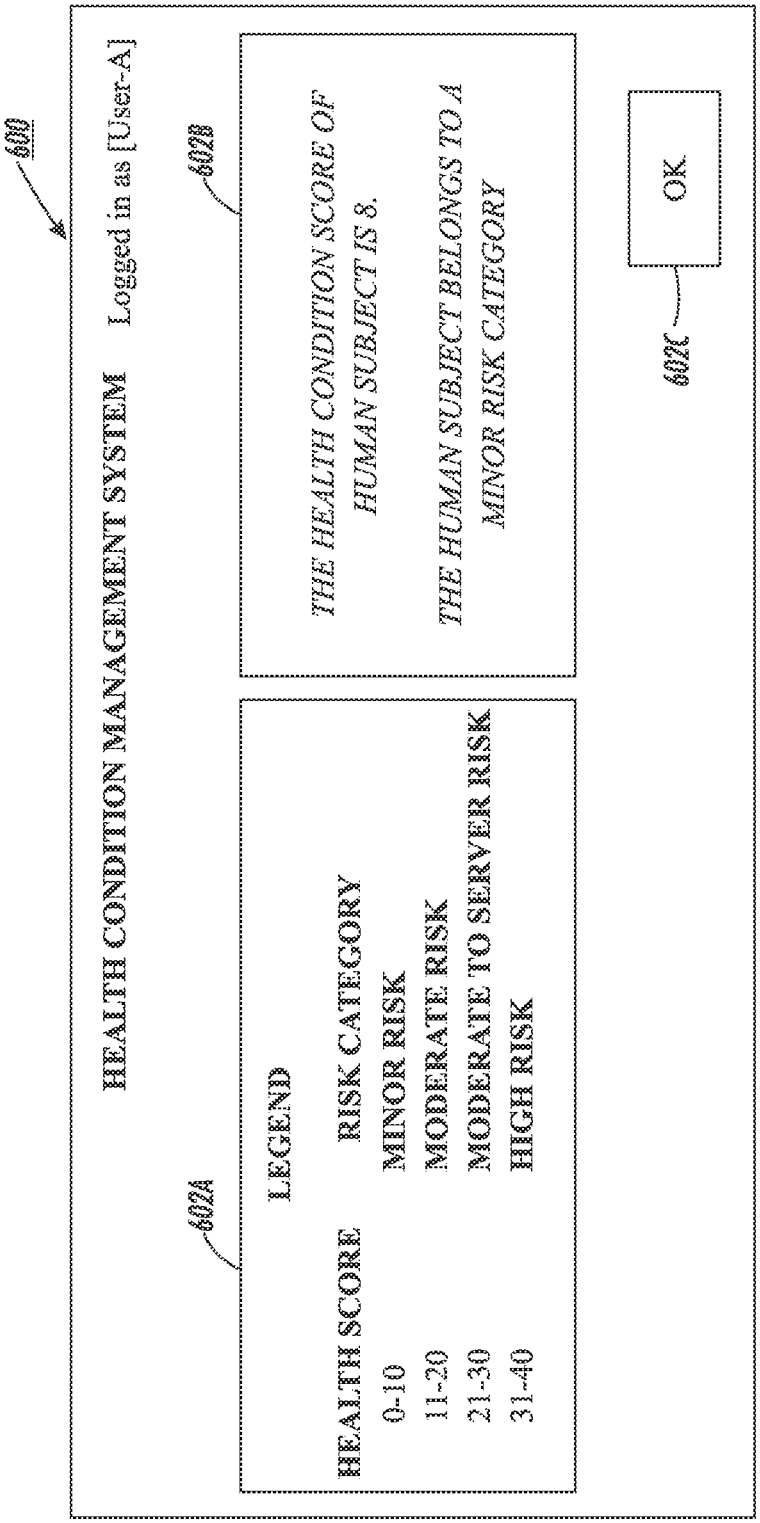
FIG. 6 is an example user-interface that may be presented to a user on a display device of a computing device to display a classification of a human subject in one or more categories indicative of a health condition of the human subject, in accordance with at least one embodiment.

FIG. 5A is an example of a user-interface 502 that may be presented on a computing device of a user, such as a User-A, to receive demographic details of the human subject, in accordance with at least one embodiment. As shown in FIG. 5A, the User-A may select the "Demographic Details" link from a region 504 and may provide various demographic details (that correspond to the demographic data view) such as age, gender, education, and job level through textboxes 506a, 506b, 506c, and 506d respectively. For example, the User-A provides age as "35 years", gender as "Male", education as "Graduate", and job level as "Working Professional". Thereafter, when the User-A selects "Next" button (depicted by 506e), a next user-interface 508 (of FIG. 5B) is presented to the User-A on the computing device.

FIG. 5B is an example of the user-interface 508 that may be presented on the computing device of the User-A to receive past diseases details of the human subject, in accordance with at least one embodiment. As shown in FIG. 5B, the User-A may select the "Past Diseases Details" link from the region 504 and may provide various past diseases details (that correspond to the past diseases data view) such as past occurrence of Hypertension, Diabetes Mellitus, Heart disease, and Celebro-Vascular accident through textboxes 510a, 510b, 510c, and 510d respectively. For example, as per input provided by the User-A, the human subject had a past occurrence of Diabetes Mellitus and Heart disease. Thereafter, when the User-A selects "Next" button (depicted by 510e), a next user-interface 512 (of FIG. 5C) is presented to the User-A on the computing device.

Figure 5C:
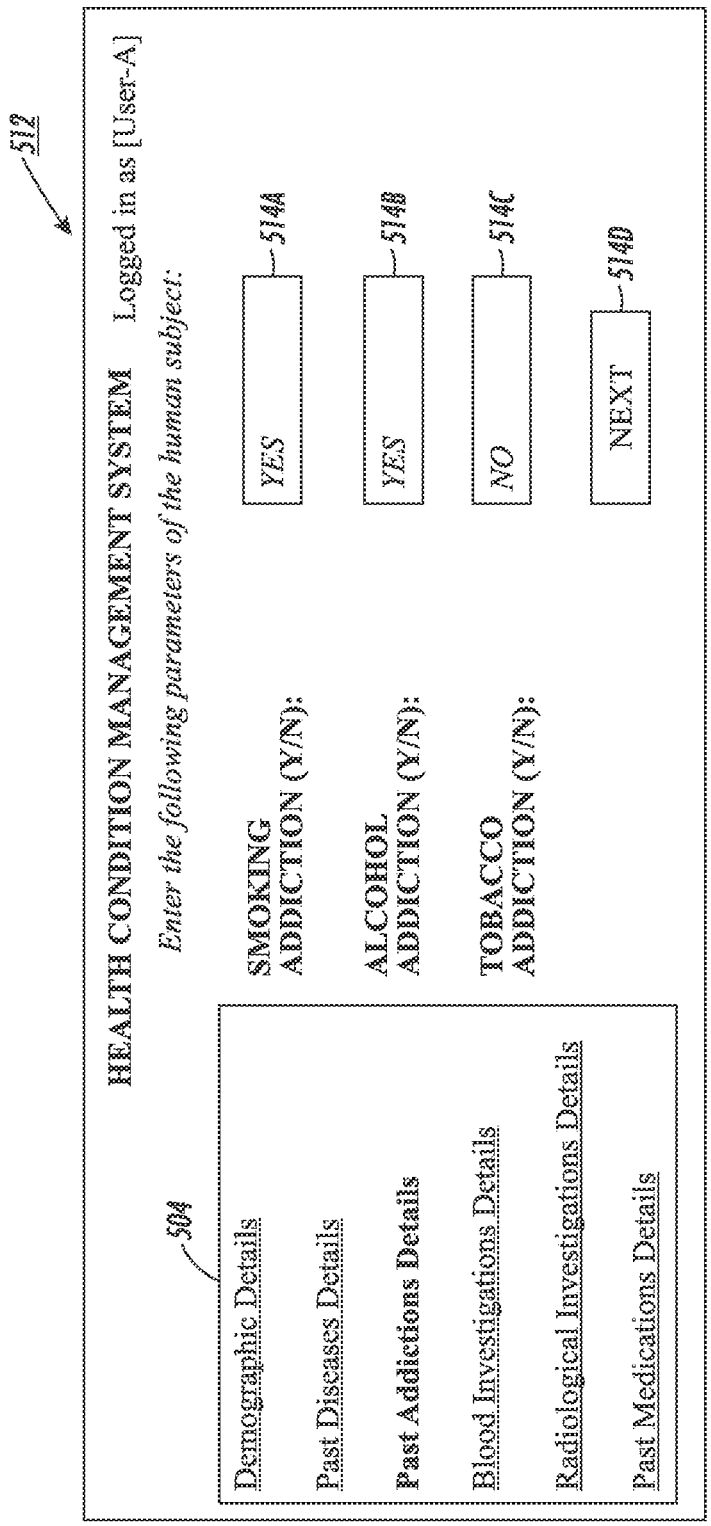

FIG. 5C is an example of the user-interface 512 that may be presented on the computing device of the User-A to receive past addictions details of the human subject, in accordance with at least one embodiment. As shown in FIG. 5C, the User-A may select the "Past Addictions Details" link from the region 504 and may provide various past addictions details (that correspond to the past addictions data view) such as Smoking Addiction, Alcohol Addiction, and Tobacco Addiction through textboxes 514a, 514b, and 514c, respectively. For example, as per input provided by the User-A, the human subject has smoking and alcohol addictions. Thereafter, when the User-A selects "Next" button (depicted by 514d), a next user-interface 516 (of FIG. 5D) is presented to the User-A on the computing device.

Figure 5D:
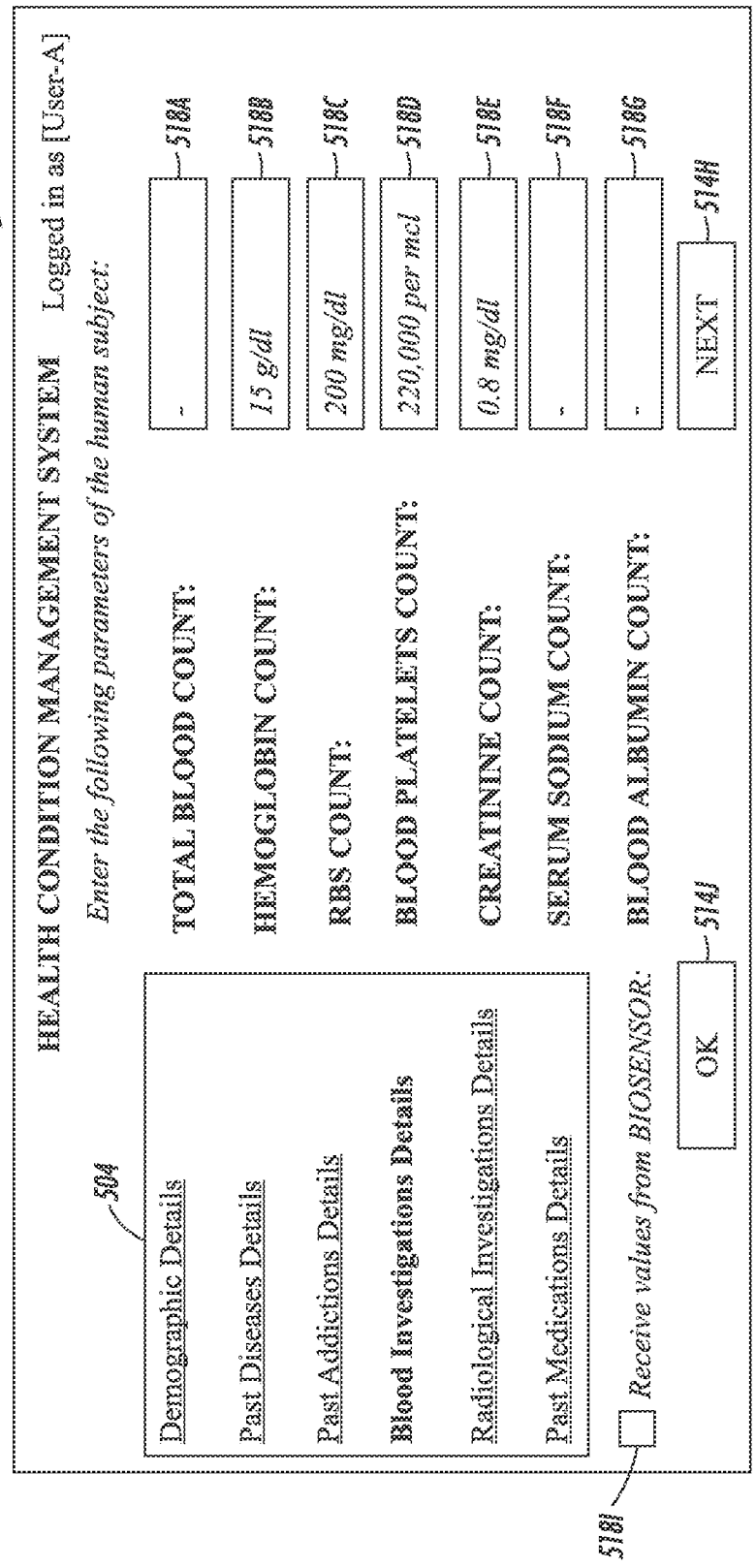

FIG. 5D is an example of the user-interface 516 that may be presented on the computing device of the User-A to receive blood investigations details of the human subject, in accordance with at least one embodiment. As shown in FIG. 5D, the User-A may select the "Blood Investigations Details" link from the region 504 and may provide various blood investigations details (that correspond to the blood investigations data view) such as Total Blood Count, Hemoglobin Count, RBS Count, Blood Platelets Count, Creatinine Count, Serum Sodium Count, and Blood Albumin Count through textboxes 518a, 518b, 518c, 518d, 518e, 518f, and 518g respectively. For example, the blood investigations details provided by the User-A include Hemoglobin Count of 16/dl, RBS Count of 200 mg/dl, Blood Platelet Count of 220,000 per mcl, and Creatinine Count of 0.8 mg/dl. In an embodiment, the user may not provide values of all the parameters related to Blood Investigations due to either unavailability of the values or the values being not required to determine the human subject's current state of health. For example, as shown in FIG. 5D, the User-A does not provide values for Total Blood Count, Hemoglobin Count, Serum Sodium Count, and Blood Albumin Count. In an embodiment, the values of the parameters related to Blood Investigations such as Hemoglobin Count, RBS Count, Blood Platelet Count, etc. may be measured using one or more sensors or blood work test (e.g., a biosensor), which may be connected to the computing device of the User-A. For example, the User-A may connect the one or more sensors (e.g., a biosensor) to his/her computing device and thereafter measure the values of Blood Investigation parameters using the one or more sensors. When the User-A selects a checkbox 518i and clicks an OK button 518j, the measured values of the Blood Investigation parameters may be received from the one or more sensors and displayed in the respective fields within the user-interface 516. Thereafter, when the User-A selects "Next" button (depicted by 518h), a next user-interface 520 (of FIG. 5E) is presented to the User-A on the computing device.

A person skilled in the art would appreciate that though the user-interface 516 depicts a scenario of receiving values of the parameters related to Blood Investigations from a single biosensor, the scope of the disclosure should not be limited to a single biosensor. In an embodiment, the values of such parameters may be received from multiple biosensors. Further, a person skilled in the art would appreciate that the user-interface 516 may also receive other physiological parameters related to the human subject such as, but not limited to, blood pressure, heart rate, blood carbon dioxide concentration, body temperature, etc.

Figure 5E:
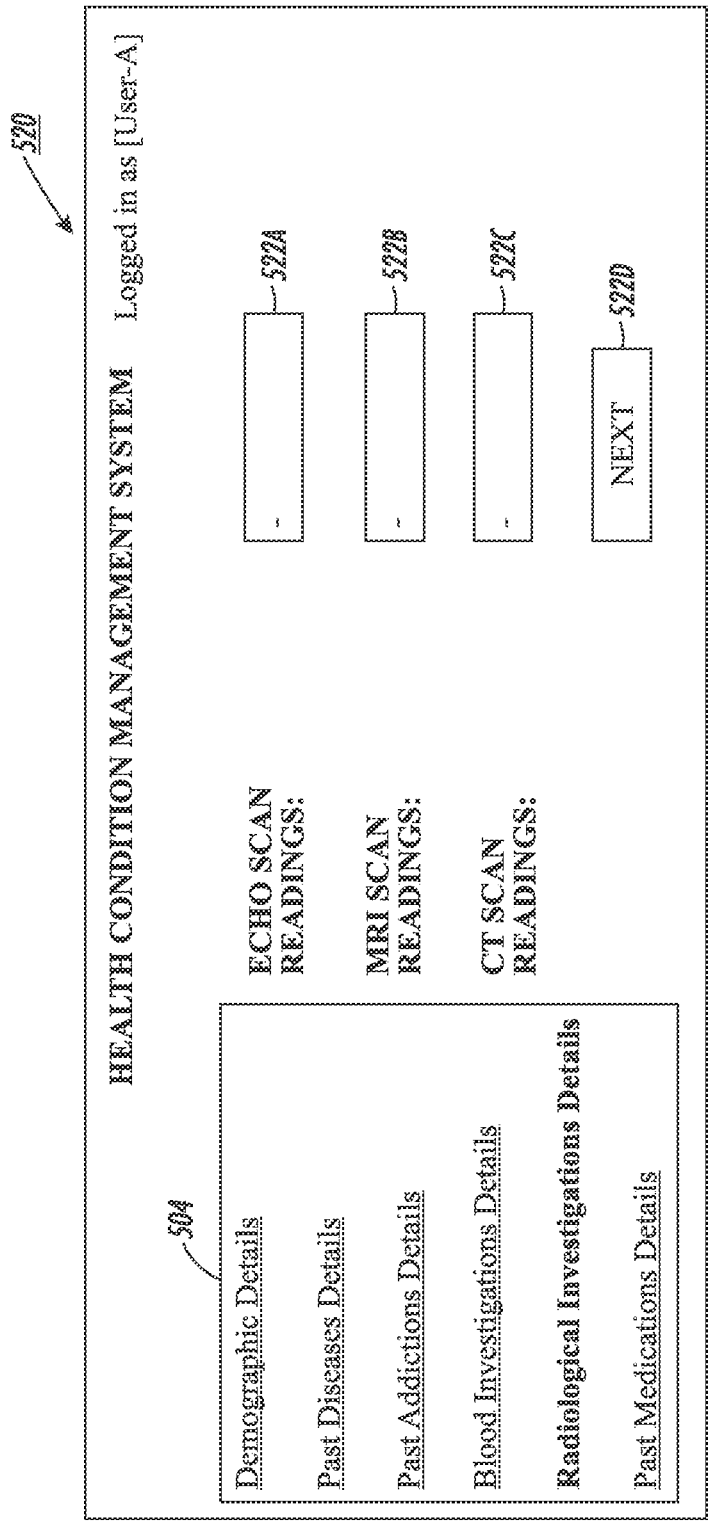

FIG. 5E is an example of the user-interface 520 that may be presented on the computing device of the User-A to receive radiological investigations details of the human subject, in accordance with at least one embodiment. As shown in FIG. 5E, the User-A may select the "Radiological Investigations Details" link from the region 504 and may provide various radiological investigations details (that correspond to the radiological investigations data view) such as Echo Scan Readings, MRI Scan Readings, and CT Scan Readings through textboxes 522a, 522b, and 522c respectively. In an embodiment, the user may not provide values of all the parameters due to either non-availability of the values or the values not being required to determine the human subject's current state of health. For example, the User-A does not provide values for the Echo Scan Readings, MRI Scan Readings, and CT Scan Readings. Thereafter, when the User-A selects "Next" button (depicted by 522d), a next user-interface 524 (of FIG. 5F) is presented to the User-A on the computing device.

Figure 5F:
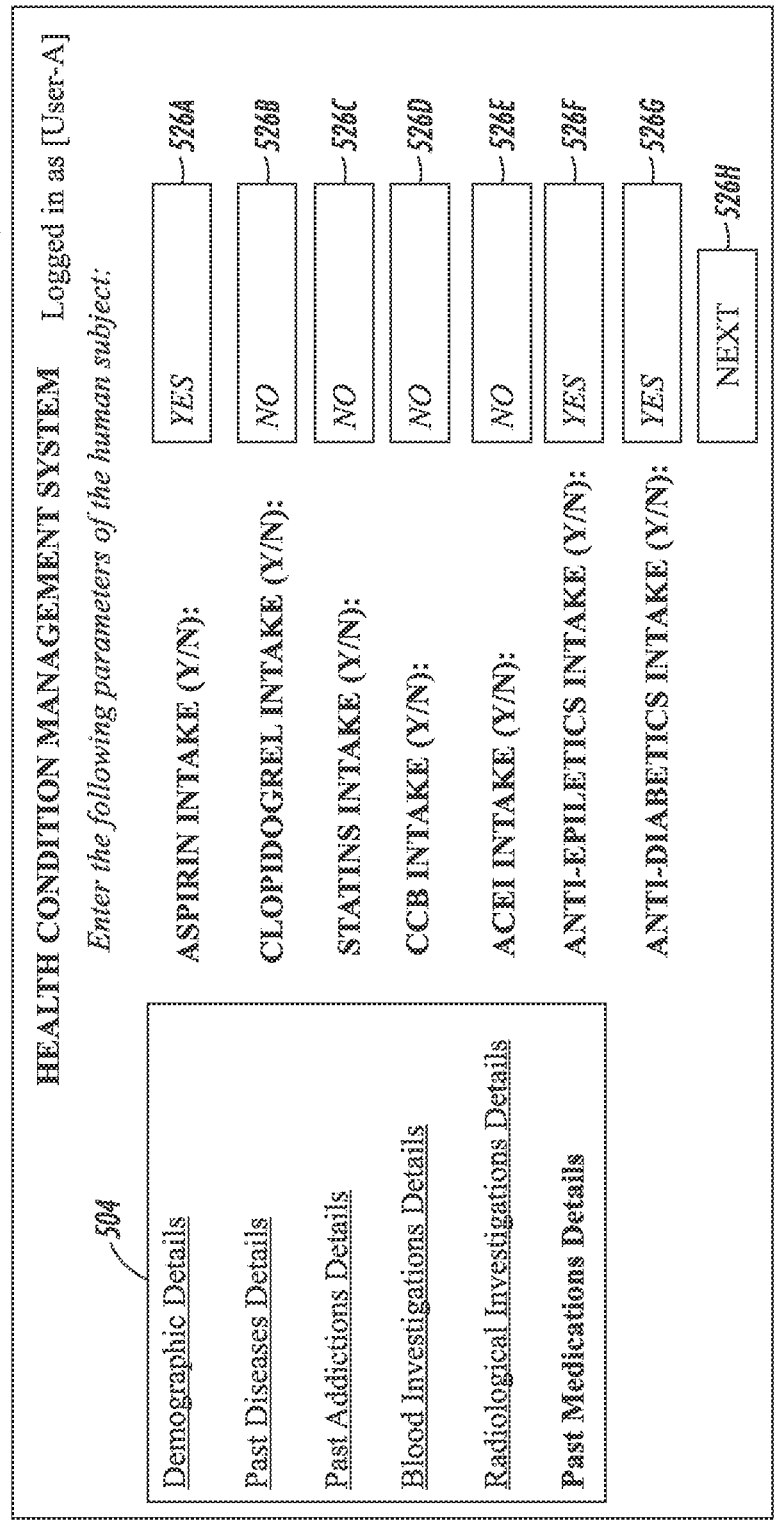

FIG. 5F is an example of the user-interface 524 that may be presented on the computing device of the User-A to receive past medications details of the human subject, in accordance with at least one embodiment. As shown in FIG. 5F, the User-A may select the "Past Medications Details" link from the region 504 and may provide various past medications details (that correspond to the past medications data view) such as Aspirin intake, Clopidogrel intake, Statins intake, CCB intake, ACEI intake, Anti-Epiletics intake, and Anti-Diabetics intake through textboxes 526a, 526b, 526c, 526d, 526e, 526f, and 526g, respectively. For example, as per input provided by the User-A, the medication intake of the human subject includes Aspirin, Anti-Epileptics, and Anti-Diabetics. Thereafter, when the User-A selects "Next" button (depicted by 526h), a next user-interface 600 (of FIG. 6) is presented to the User-A on the computing device.

FIG. 6 is an example of the user-interface 600 that may be presented to the user (e.g., the User-A) on the computing device to display the classification of the human subject in the one or more categories indicative of a health condition of the human subject, in accordance with at least one embodiment. As shown in FIG. 6, the classification of the human subject in the one or more categories is displayed along with the health condition score of the human subject in a region 602b, while a legend showing a ranges of health condition scores and respective disease risk categories is displayed in a region 602a. For example, the health condition score may correspond to a stroke score of the human subject such as the NIHSS score of the human subject. As shown in region 602b, the health condition score of the human subject is eight and the corresponding risk category of the human subject is "Minor Risk Category". In an embodiment, the health condition score and the risk category determined for the human subject may be utilized to determine a treatment course, an emergency care decision, and/or a rehabilitation course for the human subject.

A person skilled in the art would appreciate that the user-interfaces depicted in FIGS. 5A-5F and FIG. 6 (i.e., 502, 508, 512, 516, 520, 524, and 600) are illustrated for the purpose of examples. The scope of the disclosure should not be limited to such example user-interfaces. The disclosure may be implemented through one or more variations of such user-interfaces.

The disclosed embodiments encompass numerous advantages. Various advantages of the disclosure include generation of a classifier from patient/human subject dataset with data of heterogeneous data types. Thus, in addition to blood investigations data, data associated with the human subjects of various other types such as, demographic data, past disease data, past medications data, etc., may be utilized to train the classifier. Such classifier may be more accurate than a classifier that does not consider such other types of clinical and non-clinical data of the human subjects, which may be correlated to a risk of stroke among the human subjects. Further, the classifier may be robust to missing values within the dataset, as using a technique such as Bayesian learning based CMF may impute most of the missing values within the dataset. Reasons for missing values within the medical record dataset may include unavailability of readings of various medical tests and improper transcription of values/data discrepancies that lead to erroneous data being removed from the dataset.

Further, creating a classifier capable of determining a health condition score of a human subject may help the medical practitioner in determining the prognosis of a disease. Accordingly, the medical practitioner may determine a further course of treatment. Additionally, the health condition score may be transmitted to the hospital authority, which based on the health condition score, may make arrangements for disposition of the human subject. As a computing device (i.e., application server) is being used to determine the health condition score, the time of the medical practitioner for determining the health condition score is reduced. The time so saved, may be used by the medical practitioner to determine the further course of action for the patient.

The disclosed methods and systems, as illustrated in the ongoing description or any of its components, may be embodied in the form of a computer system. Typical examples of a computer system include a general-purpose computer, a programmed microprocessor, a micro-controller, a peripheral integrated circuit element, and other devices, or arrangements of devices that are capable of implementing the steps that constitute the method of the disclosure.

The computer system comprises a computer, an input device, a display unit and the Internet. The computer further comprises a microprocessor. The microprocessor is connected to a communication bus. The computer also includes a memory. The memory may be Random Access Memory (RAM) or Read Only Memory (ROM). The computer system further comprises a storage device, which may be a hard-disk drive or a removable storage drive, such as, a floppy-disk drive, optical-disk drive, and the like. The storage device may also be a means for loading computer programs or other instructions into the computer system. The computer system also includes a communication unit. The communication unit allows the computer to connect to other databases and the Internet through an input/output (I/O) interface, allowing the transfer as well as reception of data from other sources. The communication unit may include a modem, an Ethernet card, or other similar devices, which enable the computer system to connect to databases and networks, such as, LAN, MAN, WAN, and the Internet. The computer system facilitates input from a user through input devices accessible to the system through an I/O interface.

In order to process input data, the computer system executes a set of instructions that are stored in one or more storage elements. The storage elements may also hold data or other information, as desired. The storage element may be in the form of an information source or a physical memory element present in the processing machine.

The programmable or computer-readable instructions may include various commands that instruct the processing machine to perform specific tasks, such as steps that constitute the method of the disclosure. The systems and methods described can also be implemented using only software programming or using only hardware or by a varying combination of the two techniques. The disclosure is independent of the programming language and the operating system used in the computers. The instructions for the disclosure can be written in all programming languages including, but not limited to "C," "C++," "Visual C++," and "Visual Basic." Further, the software may be in the form of a collection of separate programs, a program module containing a larger program or a portion of a program module, as discussed in the ongoing description. The software may also include modular programming in the form of object-oriented programming. The processing of input data by the processing machine may be in response to user commands, the results of previous processing, or from a request made by another processing machine. The disclosure can also be implemented in various operating systems and platforms including, but not limited to, "Unix," "DOS," "Android," "Symbian," and "Linux."

The programmable instructions can be stored and transmitted on a computer-readable medium. The disclosure can also be embodied in a computer program product comprising a computer-readable medium, or with any product capable of implementing the above methods and systems, or the numerous possible variations thereof.

Various embodiments of the methods and systems for classifying a human subject in one or more categories indicative of a health condition of the human subject have been disclosed. However, it should be apparent to those skilled in the art that modifications in addition to those described, are possible without departing from the inventive concepts herein. The embodiments, therefore, are not restrictive, except in the spirit of the disclosure. Moreover, in interpreting the disclosure, all terms should be understood in the broadest possible manner consistent with the context. In particular, the terms "comprises" and "comprising" should be interpreted as referring to elements, components, or steps, in a non-exclusive manner, indicating that the referenced elements, components, or steps may be present, or utilized, or combined with other elements, components, or steps that are not expressly referenced.

A person having ordinary skills in the art will appreciate that the system, modules, and sub-modules have been illustrated and explained to serve as examples and should not be considered limiting in any manner. It will be further appreciated that the variants of the above disclosed system elements, or modules and other features and functions, or alternatives thereof, may be combined to create other different systems or applications.

Those skilled in the art will appreciate that any of the aforementioned steps and/or system modules may be suitably replaced, reordered, or removed, and additional steps and/or system modules may be inserted, depending on the needs of a particular application. In addition, the systems of the aforementioned embodiments may be implemented using a wide variety of suitable processes and system modules and is not limited to any particular computer hardware, software, middleware, firmware, microcode, or the like.

The claims can encompass embodiments for hardware, software, or a combination thereof.

It will be appreciated that variants of the above disclosed, and other features and functions or alternatives thereof, may be combined into many other different systems or applications. Presently unforeseen or unanticipated alternatives, modifications, variations, or improvements therein may be subsequently made by those skilled in the art, which are also intended to be encompassed by the following claims.

The invention claimed is:

1. A system for classifying one or more human subjects in one or more categories, wherein said one or more categories are indicative of a health condition associated with said one or more human subjects, the system comprising:
   one or more micro-processors configured to:
      categorize one or more parameters associated with each of said one or more human subjects in one or more data views based on at least a data type of each of said one or more parameters, wherein a data view corresponds to a first data structure storing a set of parameters, categorized in said data view, associated with each of said one or more human subjects;
      transform said one or more data views to a second data structure, wherein said second data structure is representative of said set of parameters across each of said one or more data views,
      wherein within the second data structure, correlated information across said one or more data views is preserved, while data view specific information, which is present in a specific data view and is not correlated to information present in other data views, is not preserved in the second data structure,
      wherein transforming said one or more data views includes combining said one or more data views into a collective matrix, and factorizing the collective matrix into the second data structure,
      wherein the second data structure is represented by a matrix with a dimension that is lower than a corresponding dimension of the collective matrix; and
      train a classifier based on said second data structure, wherein said classifier classifies said one or more human subjects in said one or more categories; and
   a transceiver configured to send said classification of said one or more human subjects in said one or more categories to a computing device, wherein said classification of said one or more human subjects is displayed on a display device of said computing device through a user-interface.

2. The system of claim 1, wherein said data type corresponds to at least one of a categorical data type, a binary data type, or a numerical data type.

3. The system of claim 1, wherein each of said one or more categories corresponds to a range of a stroke score.

4. The system of claim 1, wherein said one or more data views correspond to at least one of a demographic data view, a past diseases data view, a past addictions data view, a blood investigations data view, a radiological investigations data view, or a past medications data view.

5. A method for classifying one or more human subjects in one or more categories, wherein said one or more categories are indicative of a health condition associated with said one or more human subjects, the method comprising:
categorizing, by one or more micro-processors, one or more parameters associated with each of said one or more human subjects in one or more data views based on at least a data type of each of said one or more parameters, wherein a data view corresponds to a first data structure storing a set of parameters, categorized in said data view, associated with each of said one or more human subjects;
transforming, by said one or more micro-processors, said one or more data views to a second data structure, wherein said second data structure is representative of said set of parameters across said one or more data views,
wherein within the second data structure, correlated information across said one or more data views is preserved, while data view specific information, which is present in a specific data view and is not correlated to information present in other data views, is not preserved in the second data structure,
wherein transforming said one or more data views includes combining said one or more data views into a collective matrix, and factorizing the collective matrix into the second data structure,
wherein the second data structure is represented by a matrix with a dimension that is lower than a corresponding dimension of the collective matrix;
training, by said one or more micro-processors, a classifier based on said second data structure, wherein said classifier classifies said one or more human subjects in said one or more categories; and
sending, by a transceiver, said classification of said one or more human subjects in said one or more categories to a computing device, wherein said classification of said one or more human subjects is displayed on a display device of said computing device through a user-interface.

6. The method of claim 5, wherein said data type corresponds to at least one of a categorical data type, a binary data type, or a numerical data type.

7. The method of claim 5, wherein each of said one or more categories corresponds to a range of a stroke score.

8. The method of claim 5, wherein said one or more data views correspond to at least one of a demographic data view, a past diseases data view, a past addictions data view, a blood investigations data view, a radiological investigations data view, or a past medications data view.

9. The method of claim 8, wherein said set of parameters categorized in said demographic data view corresponds to at least one of an age of said one or more human subjects, a gender of said one or more human subjects, an education level of said one or more human subjects, or a job type of said one or more human subjects.

10. The method of claim 8, wherein said set of parameters categorized in said past diseases data view correspond to one or more past occurrences of at least one of Hypertension, Diabetes Mellitus, Heart Disease, or Cerebro-Vascular Accident, in said one or more human subjects.

11. The method of claim 8, wherein said set of parameters categorized in said past addictions data view correspond to an addiction of at least one of smoking or alcohol in said one or more human subjects.

12. The method of claim 8, wherein said set of parameters categorized in said blood investigations data view correspond to at least one of a total blood count, a hemoglobin count, a RBS count, a blood platelet count, a creatinine count, a serum sodium count, or a blood albumin count, associated with said one or more human subjects.

13. The method of claim 8, wherein said set of parameters categorized in said radiological investigations data view correspond to at least one of an Echo scan, an MRI scan, or a CT scan, associated with said one or more human subjects.

14. The method of claim 8, wherein said set of parameters categorized in said past medications data view correspond to an intake of one or more medicines comprising at least one of Aspirin, Clopidogrel, Statins, CCB, ACEI, Anti-Epileptics, or Anti-Diabetics, by said one or more human subjects.

15. The method of claim 5, wherein said transformation is based on one or more multi-view learning techniques comprising at least one of a Collective Matrix Factorization (CMF) technique, a Principal Component Analysis (PCA) technique, a Non-negative Matrix Factorization (NMF) technique, a Canonical Correlation Analysis technique (CCA), or an Inter-Battery Factor Analysis (IBFA) technique.

16. The method of claim 5, wherein said transformation corresponds to a decomposition of said one or more data views into said second data structure by utilizing a Bayesian technique.

17. The method of claim 5, wherein said second data structure preserves common information among said one or more data views and discards a data view specific information among said one or more data views.

18. The method of claim 5, wherein said classifier is trained based on one or more machine learning techniques comprising at least one of a Support Vector Machine (SVM), a Logistic Regression, a Bayesian Classifier, a Decision Tree Classifier, or a Copula-based Classifier, a K-Nearest Neighbors (KNN) Classifier, or a Random Forest (RF) Classifier.

19. The method of claim 5 further comprising determining, by said one or more micro-processors at least one of a treatment course, a rehabilitation course, a medical complication prediction, or an emergency care decision, for a human subject, based on said classification of said human subject in said one or more categories.

20. A computer program product for use with a computing device, the computer program product comprising a non-transitory computer readable medium, the non-transitory computer readable medium stores a computer program code for classifying one or more human subjects in one or more categories, wherein said one or more categories are indicative of a health condition associated with said one or more human subjects, the computer program code is executable by one or more micro-processors in the computing device to:
categorize one or more parameters associated with each of said one or more human subjects in one or more data views based on at least a data type of each of said one or more parameters, wherein a data view corresponds to a first data structure storing a set of parameters, categorized in said data view, associated with each of said one or more human subjects;

transform said one or more data views to a second data structure, wherein said second data structure is representative of said set of parameters across said one or more data views, wherein within the second data structure, correlated information across said one or more data views is preserved, while data view specific information, which is present in a specific data view and is not correlated to information present in other data views, is not preserved in the second data structure, wherein transforming said one or more data views includes combining said one or more data views into a collective matrix, and factorizing the collective matrix into the second data structure, wherein the second data structure is represented by a matrix with a dimension that is lower than a corresponding dimension of the collective matrix;

train a classifier based on said second data structure, wherein said classifier classifies said one or more human subjects in said one or more categories; and send, by a transceiver, said classification of said one or more human subjects in said one or more categories to a second computing device, wherein said classification of said one or more human subjects is displayed on a display device of said second computing device through a user-interface.

* * * * *